(12) United States Patent
Hoffman et al.

(10) Patent No.: US 11,871,731 B2
(45) Date of Patent: Jan. 16, 2024

(54) TRANSPLANTATION METHOD TO INCREASE THE ESTABLISHMENT RATE OF HUMAN TUMORS IN IMMUNODEFICIENT MICE

(71) Applicant: AntiCancer, Inc., San Diego, CA (US)

(72) Inventors: Robert M. Hoffman, San Diego, CA (US); Chihiro Hozumi, Narita (JP)

(73) Assignee: ANTICANCER, INC., San Diego, CA (US)

( * ) Notice: Subject to any disclaimer, the term of this patent is extended or adjusted under 35 U.S.C. 154(b) by 628 days.

(21) Appl. No.: 16/523,848

(22) Filed: Jul. 26, 2019

(65) Prior Publication Data

US 2020/0029540 A1    Jan. 30, 2020

Related U.S. Application Data

(60) Provisional application No. 62/711,459, filed on Jul. 27, 2018.

(51) Int. Cl.
*A01K 67/027* (2006.01)
*G01N 33/574* (2006.01)
*A01K 67/02* (2006.01)

(52) U.S. Cl.
CPC .......... *A01K 67/0275* (2013.01); *A01K 67/02* (2013.01); *G01N 33/57407* (2013.01); *A01K 2207/12* (2013.01); *A01K 2227/105* (2013.01); *A01K 2267/03* (2013.01)

(58) Field of Classification Search
CPC ............ A01K 2207/12; A01K 2207/30; A01K 67/0271
USPC ............................................................ 800/3
See application file for complete search history.

(56) References Cited

PUBLICATIONS

Murata (2020, in vivo, 34:3241-3245).*
Wang (1999, Int. J. Cancer, 51:992-995).*
Hoffman (1999, Investigational New Drugs, 17:343-359).*
Fu (1992, PNAS, 89:5645-5649).*
Kuo (1995, PNAS, 12085-12089).*
Hughes (published online Mar. 2018, Br J Radiol 2019; 92: 20170955, 12 pages.*
Strodtbeck, "Physiology of wound healing." Newborn and infant nursing reviews 1.1 (2001): 43-52.*
Bugbee, "Absolute and relative gas concentration: understanding oxygen in air." Feb. 27, 2006: 1-9.*

* cited by examiner

*Primary Examiner* — Valarie E Bertoglio
(74) *Attorney, Agent, or Firm* — Barry Choobin; Patent 360

(57) ABSTRACT

A transplantation method to increase the establishment rate of human tumors in immunodeficient mice. A pocket is created in the mouse and the tumor and surrounding tissues are implanted in the pocket. The pocket is left open to oxygenate the tumor and surrounding tissues.

12 Claims, 1 Drawing Sheet

TRANSPLANTATION METHOD TO INCREASE THE ESTABLISHMENT RATE OF HUMAN TUMORS IN IMMUNODEFICIENT MICE

CROSS REFERENCE TO RELATED APPLICATION[S]

This application claims priority to U.S. Provisional Patent Application entitled "TRANSPLANTATION METHOD TO INCREASE THE ESTABLISHMENT RATE OF HUMAN TUMORS IN IMMUNODEFICIENT MICE," Ser. No. 62/711,459, filed Jul. 27, 2018, the disclosure of which is hereby incorporated entirely herein by reference.

BACKGROUND OF THE INVENTION

Technical Field

Patient tumors have been transplanted in immunodeficient mice since 1969. However, there has generally been low establishment rate. Most patient tumors don not grow. Generally, only the highly malignant, un-pretreated tumors grow in immunodeficient mice. Thus, most patients are precluded from having a mouse model for their tumor and the resulting individualized precision treatment that a mouse model could provide.

Therefore, it is an object of the present invention to provide an improved method for establishment of patient tumors in immunodeficient mice.

DISCLOSURE OF THE INVENTION

The present invention relates to a method of transplanting a tumor of a patient in an immunodeficient mouse comprising: making at least one incision in the immunodeficient mouse, wherein at least one pocket is formed; and inserting at least one fragment comprising the tumor and surrounding tissues of the tumor into the at least one pocket, whereby a macro- and micro-environment of the tumor and the surrounding tissues in the immunodeficient mouse resembles that of the patient. The surrounding tissues may comprise fat tissue and/or necrotic tissue. The tumor type may be selected from the group consisting of breast cancer, ovarian cancer, uterine cancer, cervical cancer, and/or lung cancer. The at least one incision may be left open, thereby allowing the tumor and surrounding tissues to be oxygenated. Two pockets may be formed. The at least one incision may have an incision length in the range of from about 1 mm to about 15 mm. The incision length may be in the range of from about 3 mm to about 5 mm. The at least one fragment may have a fragment length in the range of from about 1 mm to about 10 mm. The fragment length may be about 10 mm. The at least one fragment may have a fragment width in the range of about 3 mm to about 5 mm. The at least one fragment may be rectangular in shape. Two fragments may be inserted into the at least one pocket. The immunodeficient mouse may be a nude mouse. Two incisions may be made.

The foregoing and other features and advantages of the present invention will be apparent from the following more detailed description of the particular embodiments of the invention, as illustrated in the accompanying drawings.

BRIEF DESCRIPTION OF THE DRAWINGS

A more complete understanding of the present invention may be derived by referring to the detailed description and claims when considered in connection with the Figures, wherein like reference numbers refer to similar items throughout the Figures, and:

DETAILED DESCRIPTION OF EMBODIMENTS OF THE INVENTION

A transplantation method to increase the establishment rate of patient tumors in immunodeficient mice is disclosed. The patient tumor should contain as much of its original surrounding tissues as possible, including necrotic tissue and fat tissue, when transplanted to the immunodeficient mouse. In this manner, the patient tumor maintains its original macro- and micro-environment in the immunodeficient mouse.

The method in accordance with the invention may be used with any patient solid tumor type. The tumor type may be selected from the group consisting of breast cancer, ovarian cancer, uterine cancer, cervical cancer, and/or lung cancer. The patient tumor and surrounding tissues, or fragment, for implantation into the immunodeficient mouse should be as large as possible without removing the tissues surrounding the patient tumor. No pretreatment of the fragment is required. Generally, the fragment for implantation has a fragment length in the range of from about 1 mm to about 10 mm and a fragment width in the range of from about 1 mm to 10 mm. For example, a fragment may have a fragment width in the range of from about 3 mm to about 5 mm and a fragment length of about 10 mm. The fragment may be rectangular in shape.

Generally, an immunodeficient mouse is a mouse whose immune system is not intact. A nude mouse is a type of immunodeficient mouse which lacks a thymus and therefore is deficient in T cells and can accept foreign tissue, such as human tumors.

At least one incision is made in the lower back skin of the mouse having an incision length in the range of from about 1 mm to about 15 mm, generally in the range of about 3 mm to about 5 mm to create skin flaps or pockets on the left side and/or right side of the incision. Each flap or pocket is generally large enough to insert the patient tumor and surrounding tissues. The at least one pocket is connected under the skin. A second incision may be made in the upper back skin of the mouse to create skin flaps or pockets on the left side and/or right side of the second incision.

The patient tumor and surrounding tissues (fragment) are removed from the patient. At least one fragment may be inserted into the at least one pocket. For example, two fragments may be inserted in each of a left-side and right-side pocket, i.e. two pockets, depending on the size of the immunodeficient mouse. The incision should be left open to heal by itself, allowing the fragment to be oxygenated.

Figure 1A:
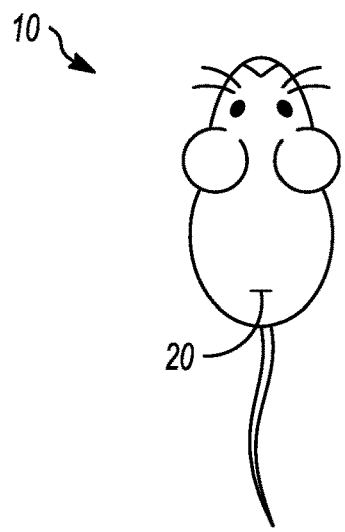
FIG. 1A shows an immunodeficient mouse in accordance with the invention.
Figure 1B:
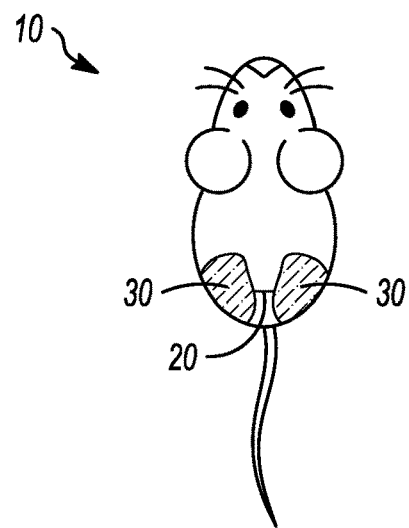
FIG. 1B shows an immunodeficient mouse, in accordance with the invention.
Figure 1C:
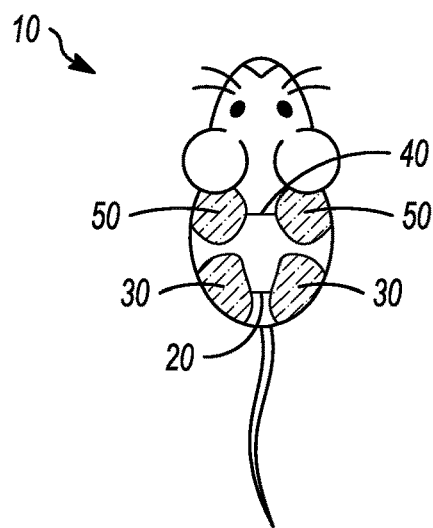
FIG. 1C shows an immunodeficient mouse in accordance with the invention.

As shown In FIGS. 1A, 1B and 1C, a first incision 20 is made on the lower back of mouse 10. Pockets 30 are created on the left and right side of first incision 20. A second incision 40 is made on the upper back of mouse 10 creating pockets 50 on the left and right side of second incision 40.

Example 1

Twenty tumors are inserted into twenty different immunodeficient mice obtained from four different doctors according to the method of the invention. Grow is defined as the patient tumor directly derived from surgery grew in the immunodeficient mouse after implantation using the method according to the invention to the extent it could be transplanted to other immunodeficient mice (establishment). No grow means no visible tumor growth could be detected 2 months after implantation. Of the twenty tumors, 18 were established and two were not established, an establishment rate of 90%.

| Cancer Type | Doctor | Establishment |
| --- | --- | --- |
| Ovarian serous | A | Grow |
| Ovarian | B | Grow |
| Breast TNBC | B | Grow |
| Ovarian | B | Grow |
| Ovarian | B | Grow |
| Breast | C | Grow |
| Lung | D | Grow |
| Lung | D | Grow |
| Ovarian | B | Grow |
| Cervical | A | Grow |
| Cervical | B | Grow |
| Uterine body | A | Grow |
| Cervical | B | Grow |
| Uterine body | B | Grow |
| Cervical | A | No Grow |
| Cervical | A | No Grow |
| Uterine body | A | Grow |
| Uterine body | B | Grow |
| Cervical | A | Grow |
| Ovarian | B | Grow |

The embodiments and examples set forth herein were presented to best explain the present invention and its practical application and to thereby enable those of ordinary skill in the art to make and use the invention. However, those of ordinary skill in the art will recognize that the foregoing description and examples have been presented for the purposes of illustration and example only. The description as set forth is not intended to be exhaustive or to limit the invention to the precise form disclosed. Many modifications and variations are possible in light of the teachings above without departing from the spirit and scope of the forthcoming claims.

The invention claimed is:

1. A method of transplanting a tumor of a patient in an immunodeficient mouse comprising:
   making at least one incision in the immunodeficient mouse, wherein at least one pocket is formed; and
   inserting at least one fragment comprising the tumor and surrounding normal tissues of the tumor into the at least one pocket, wherein the surrounding normal tissues comprises at least all normal tissues in contact with the tumor before preparing the at least one fragment, wherein the normal tissues surrounding the tumor are not removed and remain intact, wherein the surrounding normal tissues form a macro- and micro-environment of the transplanted tumor,
   wherein the at least one incision is left open, thereby allowing the tumor and surrounding tissues to be oxygenated,
   wherein the surrounding normal tissue and tumor co-implanted together are in contact with each other.

2. The method of claim 1, wherein the surrounding tissues comprise fat tissue and/or necrotic tissue.

3. The method of claim 1, wherein a tumor type is selected from the group consisting of breast cancer, ovarian cancer, uterine cancer, cervical cancer, and lung cancer.

4. The method of claim 1, wherein two pockets are formed on left and right sides of each of the at least one incision.

5. The method of claim 1, wherein the at least one incision has an incision length in the range of from 1 mm to 15 mm.

6. The method of claim 5, wherein the incision length is in the range of 3 mm to 5 mm.

7. The method of claim 1, wherein the at least one fragment has a fragment length in the range of 1 mm to 10 mm.

8. The method of claim 7, wherein the fragment length is 10 mm.

9. The method of claim 1, wherein the at least one fragment has a fragment width in the range of 3 mm to 5 mm.

10. The method of claim 1, wherein two fragments are inserted into the at least one pocket.

11. The method of claim 1, wherein the immunodeficient mouse is a nude mouse.

12. The method of claim 1, wherein two incisions are made.

* * * * *